United States Patent [19]
Kanz et al.

[11] Patent Number: 5,472,867
[45] Date of Patent: Dec. 5, 1995

[54] EX VIVO EXPANSION OF PERIPHERAL BLOOD PROGENITOR CELLS

[75] Inventors: Lothar Kanz, Freiburg; Woefram Brugger, Kirchzarten; Roland Mestepsmann, Freiburg, all of Germany

[73] Assignee: Klinkum der Albert-Ludwigs-Universitat Freiberg, Freiberg, Germany

[21] Appl. No.: 128,884

[22] Filed: Sep. 29, 1993

[30] Foreign Application Priority Data

Dec. 3, 1992 [DE] Germany ............... 42 40 635.8

[51] Int. Cl.⁶ ............... C12N 5/02; A61K 35/14
[52] U.S. Cl. ............... 435/240.25; 435/240.3; 424/85.1; 424/85.2; 424/85.5; 424/93.71; 424/144.1
[58] Field of Search ............... 435/240.2, 240.25; 424/85.1, 85.2, 85.5, 85.8, 93 V, 93.71, 144.1; 530/413

[56] References Cited

U.S. PATENT DOCUMENTS 5,199,942  4/1993  Gillis ............... 604/4

OTHER PUBLICATIONS

Berenson, R. J., et al. (1991) Blood 77: 1717–22.
Brugger, W., et al. (1992) Blood 79: 1193–1200.
Brugger, W., et al. (1993) Blood 81: 2579–84 (issued 15 May 1993).
Caux, C., et al. (1992) Blood 79: 2628–35.
Haylock, D. N., et al. (1992) Blood 80(6): 1405–12.
Leary, A. G., et al. (1988) Blood 71: 1759–63.
Moore, M. A. S. (1991) Cancer 67: 2718–26.
To, L. B., et al. (1992) Exp. Hematol. 20(6): 753, abstract No. 185, (issued Jul. 1992).
Williams, N., et al. (1992) Blood 79: 58–64.
Brugger et al., Annals of Oncology 65:40a (Oct., 1992).

Primary Examiner—Stephen G. Walsh
Assistant Examiner—David L. Fitzgerald
Attorney, Agent, or Firm—Connolly & Hutz

[57] ABSTRACT

Patients suffering from certain types of cancer are treated by high-dose chemotherapy. In order to allow a recovery a process for the ex vivo expansion of peripheral blood progenitor cells is described, wherein CD 34⁺-cells are enriched and cultivated in a medium comprising IL-1, IL-3, IL-6, EPO and SCF. The ex vivo expanded peripheral blood progenitor cells can be administered to cancer patients after chemotherapy.

12 Claims, 4 Drawing Sheets

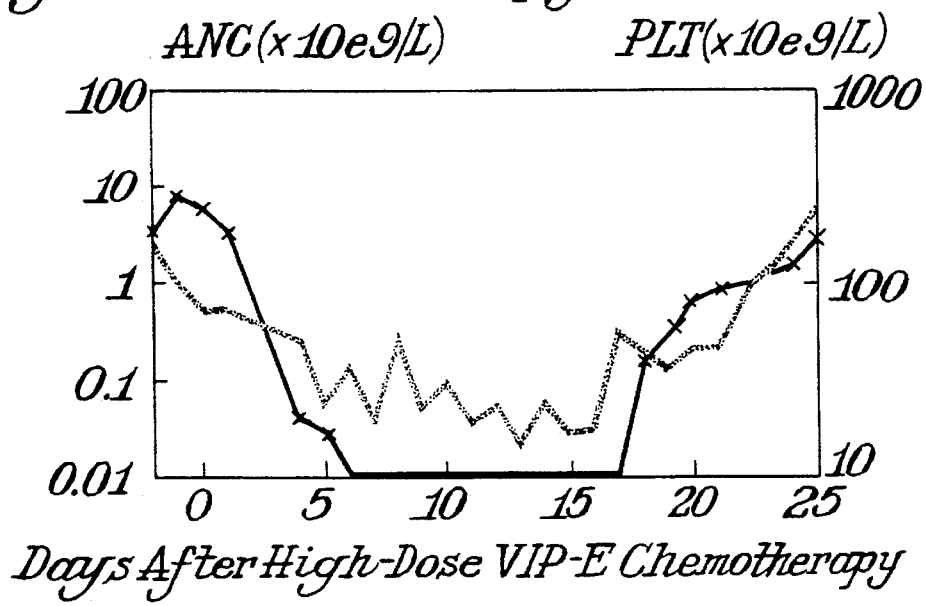
*Fig. 3a.*
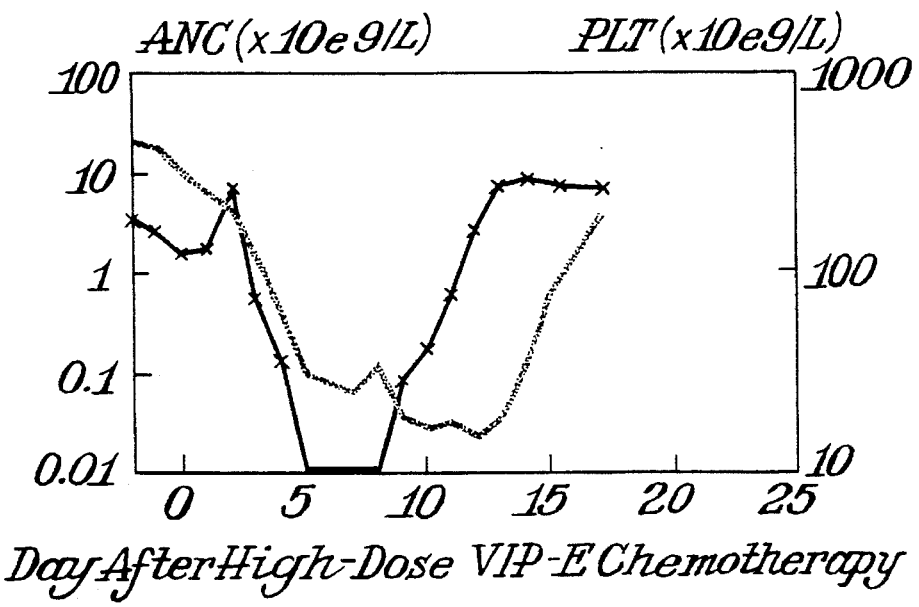
*Fig. 3b.* ANC = Granulocytes
PLT = Platelets

5,472,867

EX VIVO EXPANSION OF PERIPHERAL BLOOD PROGENITOR CELLS

FIELD OF THE INVENTION

The subject matter of the present invention is related with the therapy of patients suffering from cancer after chemotherapy. The present invention discloses a process for the ex vivo expansion of peripheral blood progenitor cells, the cells obtainable by said process, compositions which allow the amplification of peripheral blood progenitor cells, receptacles containing said composition and a method for treatment of cancer patients by administering the peripheral blood progenitor cells to the patient.

BACKGROUND AND PRIOR ART

High-dose chemotherapy is potentially curative in some chemosensitive tumors and a relationship between dose intensity and cytotoxic drugs and tumor response has been defined for several malignancies. The applicable dose of chemical agents used for the treatment of cancer is mostly limited by myeloid suppression, as well as non-haematological organ toxicity. The risk of neutropenic infection and of bleeding complications requires expensive supportive care during this period. Since, however, by an intensive treatment the probability of destroying most of the committed progenitor cells is high, generally high doses of chemotherapeutic active agents are administered.

It is therefore one object of the present invention to overcome the problems associated with high-dose chemotherapy by providing a process for the ex vivo expansion of peripheral blood progenitor cells which can be administered to patients after high-dose chemotherapy.

In their publication "Engraftment After Infusion of CD 34$^+$ Marrow Cells in Patients With Breast Cancer or Neuroblastoma" (Blood, Vol. 77, No. 8 (1991), pp. 1717–1722) Berenson et al. have described the CD 34 antigen. The CD 34 antigen is expressed by 1% to 4% of human marrow cells. Because the CD 34 antigen has not been detected on most solid tumors, a positive selection of cells expressing the CD 34 antigen may be used to provide marrow cells capable of engraftment, but depleted of tumor cells.

SUMMARY OF THE INVENTION

It is therefore an object of the present invention to provide a process for the ex vivo expansion of CD 34$^+$ peripheral blood progenitor cells. The process of the present invention for the ex vivo expansion of peripheral blood progenitor cells is characterized in that peripheral blood cells are isolated from the blood of patients suffering from cancer, the cells expressing the CD 34 antigen are enriched and cultured with a combination of haematopoietic growth factors and cytokines.

BRIEF DESCRIPTION OF THE DRAWINGS

FIG. 3(a) shows regeneration of granulocytes (ANC) and platelets (PLT) after a high-dose chemotherapy without employing peripheral blood progenitor cells (PBPC).

FIG. 3(b) shows regeneration of granulocytes (ANC) and platelets (PLT) after a high-dose chemotherapy wherein selected CD34$^+$ cells are administered.

DESCRIPTION OF THE PREFERRED EMBODIMENTS

Figure 1:
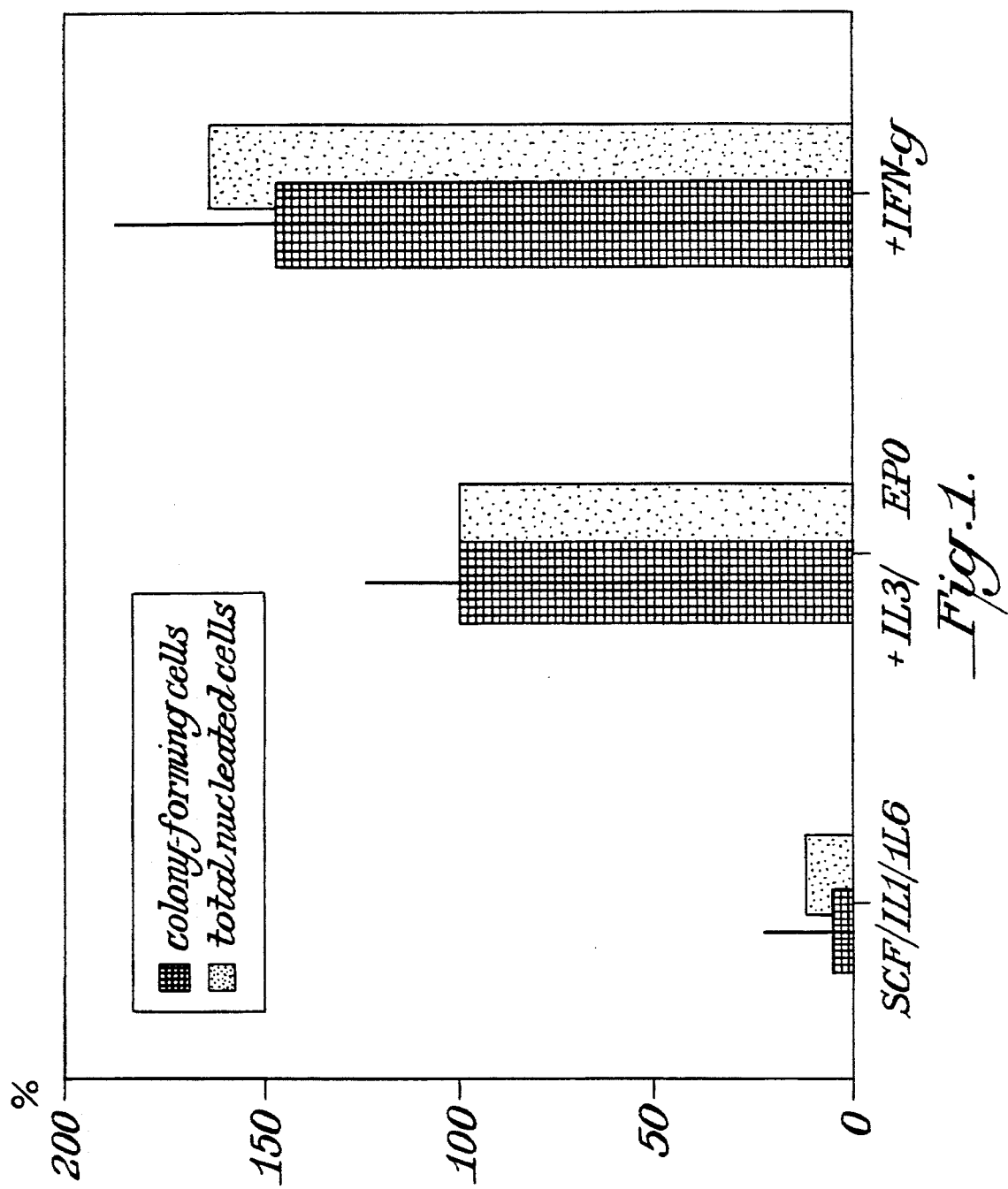
FIG. 1 shows results, in percentage, of the expansion of CD34$^+$ cells (colony forming cells) and total nucleated cells, in culture media containing, respectively, SCF/IL-1/IL-6 (left), SCF/IL-1/IL-6/IL-3/EPO (middle), and SCF/IL-1/IL-6/IL-3/EPO/INF-γ (right). As seen from the graph, the further addition of INF-γ acts to further synergistically increase the number of CD34$^+$ cells and the total nucleated cells.

The process of the present invention comprises in general the following steps:

Heparinized blood samples were obtained from the patients. Mononuclear cells (MNCs) from the apheresis product were isolated by suitable separation techniques, preferably by density gradient centrifugation over inert, non-ionizable synthetic polymer comprising the crosslinking product of epichlorohydrin and sucrose, available under the trademark FICOLL from Pharmacia, Germany. The mononuclear cells were further treated in order to enrich the CD 34$^+$-cells. This can be done by incubating the cells with a monoclonal antibody which is specific for the CD 34 antigen which is preferably biotinylated. Such monoclonal antibodies are commercially available from Dianova, Coulter, CellPro or Becton Dickinson, Germany. The cells treated with the monoclonal antibody were loaded onto an immunoaffinity column, preferably an avidin-immunoaffinity column, whereby the avidin binds the monoclonal antibodies and consequently also the CD 34$^+$-cells attached thereto. The adsorbed CD 34$^+$-cells were removed from the immunoaffinity column and resuspended in a suitable medium.

Alternatively it would also be possible to link the monoclonal antibodies specific for the CD 34 antigen directly to a solid phase (e.g. small beads) in order to fix the CD 34$^+$-cells and to separate the bound cells from the mixture.

Further it is possible to enrich the CD 34$^+$-cells by using a fluorescence activated cell sorter which is commercially available from e.g. Becton Dickinson. According to said method mobilized peripheral blood progenitor cells are reacted with an anti-CD 34-antibody having a fluorochrome label. With the help of the fluorescence activated cell sorter it is possible to separate the cells and to obtain the CD 34$^+$-cells. By this method highly purified cells can be obtained.

The enriched CD 34$^+$-cells were subsequently cultured in a suitable culturing medium. Such a medium is for example supplemented RPMI 1640 medium containing 10% fetal calf serum (Paesel, Germany). The culture medium may also contain heparinized autologous plasma, preferably in a concentration of about 1%. Single growth factors or preferably growth factor combinations were added immediately after seeding the CD 34$^+$-cells into the receptacles to be used for the cultivation like microtiter plates or culture flasks. Alternatively receptacles comprising the combination of growth factors may be prepared, which are simply inoculated with the CD 34⁺-cells. It has been found that the following growth factors were especially suitable for the process of the present invention:

Interleukin-1 (IL-1), as described by Gery I. et al., Method Enzymol. 116, 456–467 (1985); Lachmann et al., Methods Enzymol. 116, 467–497 (1985); March et al., Nature 315, 641 (1985);

Interleukin-3 (IL-3), as described in EPA 138 133, Ihle et al., Methods Enzymol. 116, 540–552 (1985); Otsuka et al., J. Immunol. 140, 2288–2295 (1988), Interleukin-6 (IL-6), as described in Brakenhoff et al., J. Immunol. 139, 4116–4121 (1987), Brakenhoff et al., J. Immunol. 143, 1175–1182 (1989), Erythropoietin (EPO) as described by Jacobs et al., Nature 313, 806–810 (1985), Sasaki et al., Methods Enzymol. 147, 328–340 (1987), Stem cell factor (SCF) as described in WO 91/05 797, Nocka et al., EMBO J. 9, 3287–3294 (1990) and Interferon-γ (IFN-γ) as described in EP 77 670, Gray et al., Nature 295, 503–508 (1982); Devos et al., Nucl. Acids Res. 10, 2487–2501 (1982); Yip et al., PNAS 79, 1820–1824 (1982) and Braude, Methods Enzymol. 119, 193–199 (1986).

The inventors found that a combination of the growth factors IL-1, IL-3, IL-6, EPO and SCF allows an effective expansion of the CD 34⁺ progenitor cells. If interferon-γ is further added, an additional enhancement can be obtained.

FIG. 1 demonstrates the synergistic effect of the growth factors SCF/IL-1/IL-6 and IL-3/EPO in the expansion of CD 34⁺-cells in a suspension culture. The addition of IFN-γ results in a further improvement of the synergistic effect of the growth factors.

The used concentration of the growth factors and cytokines respectively is within the concentration usually used showing the highest efficiency in ex vivo cultures. IL-1 can be used in concentrations which range from 10 ng/ml to 1.000 ng/ml, IL-3 is used in a concentration between 1 U/ml up to 1.000 U/ml, IL-6 is used within 10 U/ml up to 1.000 U/ml. EPO can be present in concentrations ranging from 0.1 U/ml to 10 U/ml. SCF is used between 10 ng/ml up to 1.000 ng/ml and IFN-γ can be used in a range between 1 U/ml to 1.000 U/ml.

The preferred ranges for IL-1 are between 50 ng/ml and 150 ng/ml, for IL-3 from 50 U/ml to 150 U/ml, for IL-6 from 50 U/ml up to 150 U/ml, for EPO from 0.5 U/ml to 1.5 U/ml, for SCF from 50 ng/ml to 150 ng/ml and for IFN-γ from 50 U/ml to 150 U/ml. It is within the skill of the ordinary person skilled in the art to determine the best activities of the growth factors and cytokines respectively. For the above-identified units there are international recognized standards.

It is the unexpected advantage of the process according to the invention to obtain not only a high number of nucleated cells but also a high number of colony-forming cells which means cells with a clonogenic potential. As can be seen from the enclosed FIG. 2 also other combinations of growth factors result in a high number of nucleated cells. The other combinations, however, show only lower numbers of colony-forming cells. By the combination of growth factors according to the invention a number of colony-forming cells can be obtained which is about 2.5 times higher than the number of the colony-forming cells obtainable by the combination comprising also granulocyte-macrophage colony-stimulating factor (GM).

According to a preferred embodiment of the present invention the peripheral blood progenitor cells are obtained from patients suffering from cancer which have been mobilized by conventional dose chemotherapy and colony-stimulating factors in order to combine a treatment regime with broad antitumor activity with the simultaneous mobilization of peripheral blood progenitor cells. A mobilization can be obtained by treatment of patients with a standard dose VP 16 (500 mg/m²) ifosfamide (4 g/m²) cisplatin (50 mg/m²) and optionally Epirubicin (50 mg/m²) (VIP (E) regimen) followed by the administration of G-CSF (obtainable from Amgen) at a dose of 5 µg/kg/d subcutaneously for 12 to 14 days. Alternatively it is possible to administer GM-CSF, which is for example commercially available from Sandoz AG, Basel under the trademark "Leukomax", from Sandoz AG. It is also possible to treat the cancer patients with a chemotherapy consisting of etoposide (VP 16), ifosfamide and cisplatin followed by the combined sequential administration of recombinant human interleukin-3 (rhIL-3) and recombinant human granulocytemakrophage colony-stimulating factor (rhGM-CSF).

It is especially preferred to obtain the peripheral blood progenitor cells from the patient between day 10 and day 18 after chemotherapy.

The inventors found that in some types of cancer by the mobilization also tumor cells are mobilized. Especially in the case of breast cancer and SCLC patients (newly diagnosed extensive or limited disease small cell) such a mobilization of tumor cells has been observed. If the process of the present invention is applied to patients suffering from breast cancer or SCLC, care must be taken in order to select CD 34⁺-cells and to purify the ex vivo expanded peripheral blood progenitor cells from contaminating tumor cells, preferably by a specific biological purging.

It is also especially preferred to apply the process of the present invention to such patients suffering from cancer other than breast cancer and SCLC patients (newly diagnosed extensive or limited disease small cell). The reason therefore is that obviously in patients suffering from cancer other than SCLC and breast cancer respectively, the mobilization of peripheral blood progenitor cells does not result in a tumor cell mobilization.

By the process of the present invention peripheral blood progenitor cells can be expanded ex vivo which are very valuable for the recovery of patients which have been treated by chemotherapy. Those cells are within the scope of the present invention.

The present invention encompasses also culture medium for CD 34⁺-cells comprising a combination of IL-1, IL-3, IL-6, EPO and SCF and optionally interferon-γ. The biological active compounds are used in concentrations as given above. It is possible to provide suitable receptacles equipped with a culture medium for the cultivation of peripheral blood progenitor cells comprising the above-described combination of growth factors. Such receptables can be blood bags, microtiter plates or tissue culture flasks. It is possible to prepare such receptacles ready for use in the process of the present invention.

A method for treatment of cancer patients, wherein the process of the present invention is used, is also within the scope of the present invention. In this method the ex vivo expanded CD 34⁺-cells are administered to the patient in order to provide progenitor cells capable of engraftment. The process of the present invention can be further improved by adjusting the conditions of growth for the expansion of the CD 34⁺-cells in such a manner that the peripheral blood progenitor cells can be expanded whereas tumor cells which might be within the cell preparation do not grow. Such a biological purging is also within the scope of the invention. Alternatively tumor cells may be separated from the CD 34+-cell population by treatment with immunoaffinity adsorption columns which are specific for tumor cells because of the use of monoclonal antibodies specific for tumor cells. "Biological purging" means that such culture conditions are selected which allow an expansion of the peripheral blood progenitor cells whereas the tumor cells do not grow. Since the specific conditions may vary from one tumor type to another, it is a preferred embodiment of the present invention to select the preferred growth conditions by adding a defined number of human tumor cells obtained from nude mice or from a biopsy. After defined period of times during the expansion it is checked by immunocytological and/or molecular methods whether the tumor cells are expanded or not. By using such "tracer tumor cells" it is possible to check whether the conditions of culturing result in an expansion or reduction of tumor cells.

In order to illustrate the present invention the following examples are given which should, however, not be considered to limit the scope of the present invention:

EXAMPLE 1

Mobilization of Peripheral Blood Progenitor Cells 18 patients undergoing PBPC transplantation were treated as part of their induction chemotherapy with conventional-dose VP 16 (500 mg/m$^2$), ifosfamide (4 g/m$^2$) and cisplatin (50 mg/m$^2$) (VIP) and subsequent administration of recombinant human G-CSF (Amgen, Germany) at a dose of 5 µg/kg/d subcutaneously for 10 to 14 days to mobilize PBPCs. 12 patients with solid tumors and six patients with refractory non-Hodgkins's lymphoma were included. PBPCs were collected at days 10 through 12 after VIP chemotherapy. The peripheral blood progenitor cells were obtained by leukapheresis using a so-called "small collecting chamber" (available from Baxter) on day 10–12 after the VIP chemotherapy according to the procedure as described by Brugger et al. in J. Clin. Oncol. 20, p. 1452–1459 (1992) and Brugger et al., British J. of Haematology 84, p. 402–407 (1993).

EXAMPLE 2

Culture of Harvested PBPCs

From the apheresis product mononuclear cells (MNC) were isolated by density gradient centrifugation over combined Ficoll and sodium diatrizoate (sodium diatrizoate is available under the tradename "Hypaque") (1.077 g/ml) (obtainable by Pharmacia) and washed two times in phosphate-buffered saline (PBS).

Peripheral blood or bone marrow MNC cells were grown as described in the prior art (e.g. Kanz et al., Blood, 68, 991 (1986)). MNC ($1 \times 10^5$) were immobilized in methylcellulose (0.9%) and cultured in supplemented IMDM with 30% fetal calf serum (Paesel, Germany).

EXAMPLE 3

Positive Selection of CD 34+-cells from Harvested PBPCs by Immunoaffinity Adsorption Columns Mononuclear cells (MNCs) were incubated with a biotinylated IgM anti-CD 34 monoclonal antibody, washed and loaded onto an avidin-immunoaffinity column. Adsorbed CD 34+-cells (target cell population) were removed from the avidin column and resuspended in RPMI 1640 medium (Seromed, Germany) supplemented with 3 mmol/L glutamine and $5 \times 10^{-5}$ mol/L β-mercaptoethanol (Sigma, Germany).

EXAMPLE 4

Expansion of Enriched CD 34+-cells in Suspension Culture

Enriched CD 34+-cells were cultured in 96-well flatbottom microtiter plates at 0.5 to $15 \times 10^3$/mL in supplemented RPMI 1640 medium containing 10% fetal calf serum or various concentrations of autologous plasma, respectively. The combination of growth factors as described above was added immediately after seeding the CD 34+-cells into the microtiter plates (total volume, 200 µL/well). Quadruplicate cultures of each of the 36 growth factor combinations tested were established. The following haematopoietic growth factors and cytokines were used: IL-1, IL-3, GM-CSF, IL-6, M-CSF, LIF, IFN-γ, SCF. Growth factors like IL-1, G-CSF, GM-CSF, M-CSF, IFN-γ and SCF at a concentration of 100 ng/mL (IL-1, G-CSF, GM-CSF, M-CSF, IFN-γ and SCF) or at a concentration of 100 U/mL (IL-3 and IL-6) or 10 ng/mL for LIF respectively. Erythropoietin was used at 1 U/mL. Cells were incubated for up to 28 days at 37° C. in 5% $CO_2$ without additional feeding of growth factors or medium. For analysis each well was resuspended and washed in RPMI 1640 to remove residual growth factors. Viability of cells was assessed by trypan blue dye exclusion as well as by flow cytometric staining with propidium iododide.

EXAMPLE 5

Large-scale Expansion of Enriched CD 34+-cells

Scaled-up expansion of enriched CD 34+-cells from the leukapheresis products of two different patients (1 patient with limited-disease small cell lung cancer and 1 patient with a refractory non-Hodgkin's lymphoma) were performed in 250 mL tissue culture flasks in 1% heparinized autologous plasma. A 100 mL culture of CD 34+-cells was established at $1.5 \times 10^4$ CD 34+-cells/mL. The cells were incubated for 21 days without further addition of any growth factors. Serial samples of cells were removed at different time points and analyzed with respect to morphology, immunophenotype, and colony-forming capacity.

EXAMPLE 6

Clonogenic Assays for Myeloid (Colony-forming Unit-granulocyte-macrophage [CFU-GM]), Erythroid (Burst-forming Unit-erythroid [BFU-E]), and Multilineage (CFU-granulocyte, Erythrocyte, Monocyte, Megakaryocyte [CFU-GEMM]) Progenitors Unseparated MNCs from the leukapheresis product, enriched CD 34+-cells as well as expanded cells were grown in 0.5% methylcellulose as described in Kanz et al., Blood 68, 991 (1986). Unseparated MNCs were cultured at $1 \times 10^5$/mL in 30% FCS. Positively enriched CD 34+-cells as well as expanded cells were cultured at three different cell concentrations ($5 \times 10^3$/mL, $1.5 \times 10^4$/mL and $5 \times 10^4$/mL). The assay was found to be linear up to a seeded cell number of $1.5 \times 10^4$/mL. All semisolid cultures were performed in duplicate and stimulated with 100 ng/mL SCF, 100 ng/mL IL-1β, 100 ng/mL GM-CSF, 20 U/mL IL-3, 100 U/mL IL-6 and EPO (1 U/mL).

The absolute number of CFU-GM, BFU-E and CFU-GEMM grown at each time point during the liquid culture was calculated by multiplying their incidence (per cells seeded in methylcellulose) by the number of living nucleated cells present in each liquid culture.

EXAMPLE 7

Dual Color or Triple-color Flow Cytometry

PB MNCs, enriched CD 34$^+$-cells, as well as expanded nucleated cells from suspension cultures were incubated with anti-CD 34 fluorescein (FITC)-conjugated of phycoerythrin (PE)-conjugated monoclonal antibodies and/or anti-CD 33-PE, anti-CD 38-PE, anti-CD 14-FITC, anti-CD 11b-FITC, anti-CD 15-FITC, anti-CD 3-PerCP, or anti-HLA-DR-PerCP conjugated monoclonal antibodies for 30 minutes at 4° C. Cells were analyzed by flow cytometry using a FACScan analyzer (Becton Dickinson) equipped with a filter set for FITC-PE dual-color fluorescence. Data acquisition was performed with FACScan Lysis II research software. Each measurement included 30,000 cells.

EXAMPLE 8

Immunocytology of Expanded Cells

Enriched CD 34$^+$-cells as well as expanded nucleated cells were attached to alcian blue-coated slides and fixed in 0.05% glutaraldehyde as described by Brugger et al. (Blood, 80, p. 1629 (1992)). For analysis, the following mouse monoclonal antibodies were used: anti-CD 34, anti-CD 33, anti-HLA-DR, and anti-CD 38 (all obtainable from Becton Dickinson). A peroxidase-antiperoxidase (PAP) technique was applied, followed by postfixation with $OsO_4$.

Figure 2:
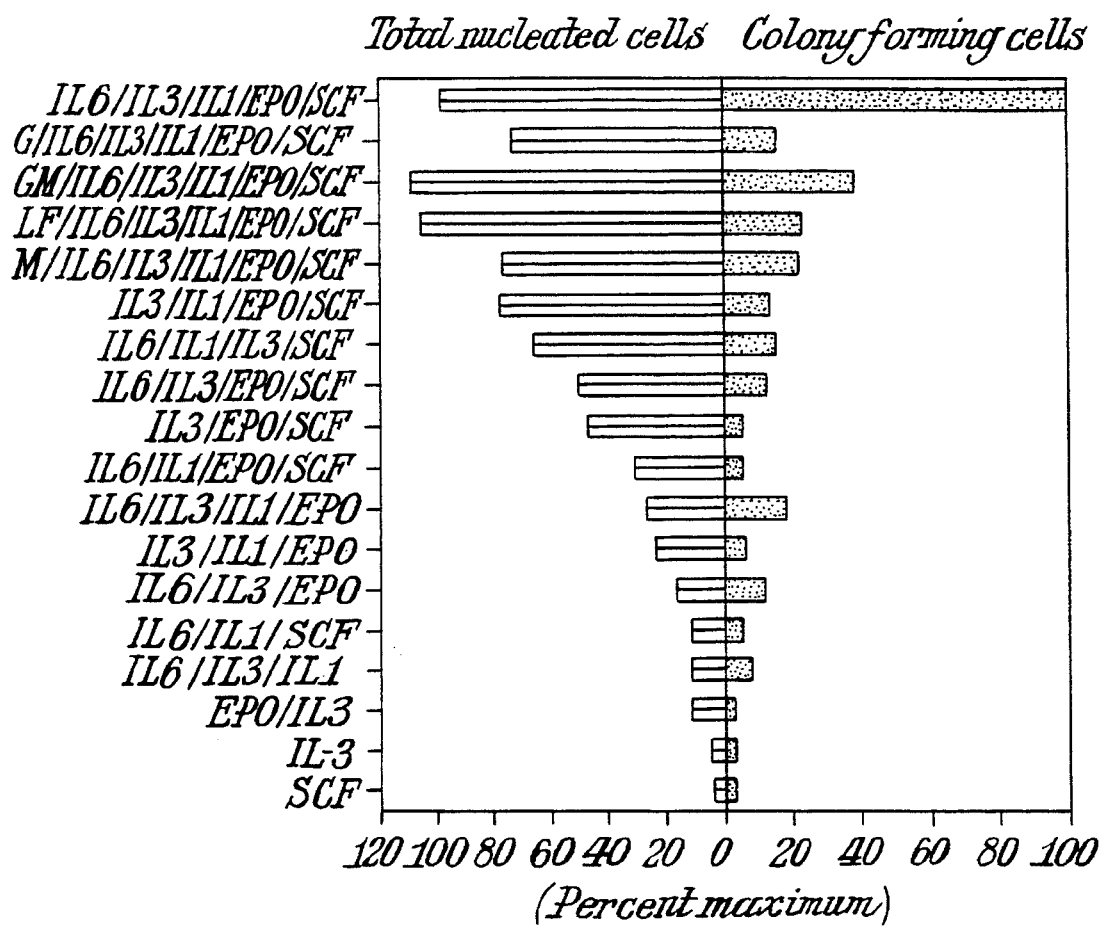
FIG. 2 shows the results, percent maximum, of expansion of CD34$^+$ cells (colony forming cells) and total nucleated cells in culturing media containing growth factors, cytokines, or combinations of growth factors and cytokines.

The results of the examples are summarized in FIGS. 1 and 2.

EXAMPLE 9

Administration of Ex Vivo Expanded Cells to Patients

Figure 3C:
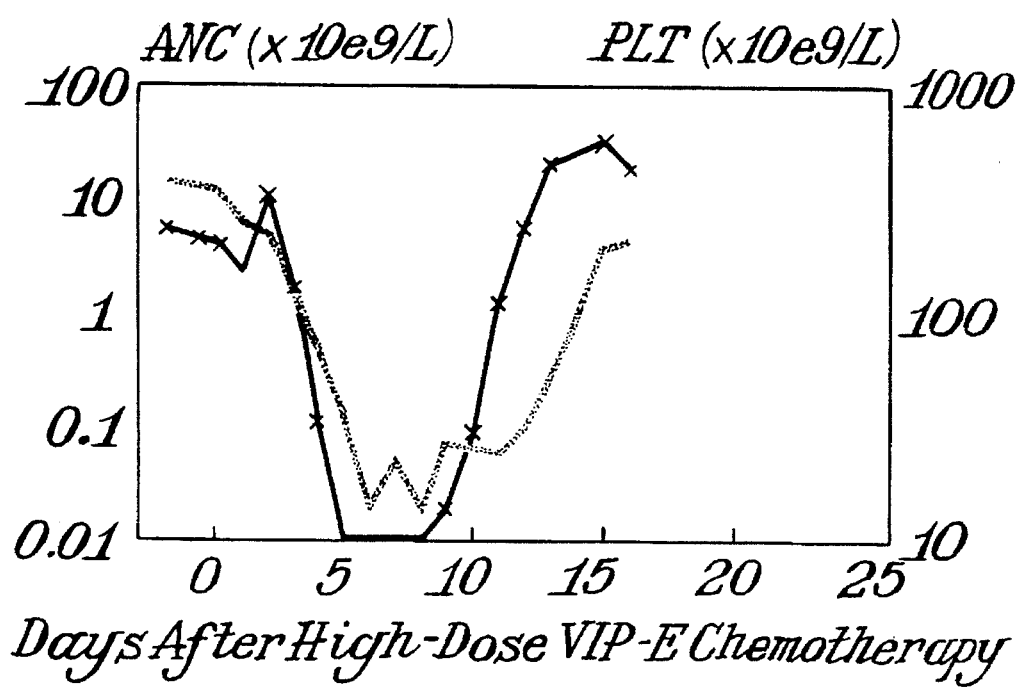
FIG. 3(C) shows regeneration of granulocytes (ANC) and platelets (PLT) after a high-dose chemotherapy wherein CD34+ cells which are ex vivo expanded in accordance with the invention are administered.

The process of the present invention has been used in order to treat three pilot-patients with cancer with advanced malignancy (two patients suffered from sarcoma and one patient suffered from a carcinoma of unknown primary localization). The peripheral blood progenitor cells have been expanded as described above, although the cytokine concentrations were slightly lower than given above. It was found that by the method of the present invention a 20-fold up to 100-fold expansion could be achieved. The expanded cells were washed and subsequently administered to the patient. The results of this study are summarized in FIG. 3. Comparison of FIGS. 3(a)–3(c) reflects that the ex vivo expanded cells of the invention achieve favorable regeneration of the blood comparable to selected CD34+ cells.

We claim:

1. A process for ex vivo expansion of peripheral blood progenitor cells, which comprises isolating peripheral blood cells from the blood, enriching blood progenitor cells expressing the CD34 antigen, and culturing the enriched blood progenitor cells in a suitable cell growth medium to which has been added a combination of hematopoietic growth factors and cytokines consisting essentially of interleukin-1, interleukin-3, interleukin-6, erythropoietin, and stem cell growth factor.

2. The process of claim 1, wherein the peripheral blood cells are isolated by density gradient centrifugation.

3. The process of claim 1, wherein the peripheral blood cells are isolated by reaction with an anti-CD34 antibody, followed by immunoaffinity separation from non-reacted cells.

4. The process of claim 1, wherein the blood is obtained from a cancer patient.

5. The process of claim 4, wherein the cancer patient has received chemotherapy prior to the blood being obtained, the chemotherapy comprising administration of etoposide, isofamide and cisplatin.

6. The process of claim 5, wherein the prior chemotherapy is followed by combined or sequential administration of recombinant human interleukin-3 and recombinant human granulocyte-macrophage colony stimulating factor prior to the blood being obtained.

7. A process for ex vivo expansion of peripheral blood progenitor cells, which comprises isolating peripheral blood cells from the blood, enriching blood progenitor cells expressing the CD34 antigen, and culturing the enriched blood progenitor cells in a suitable cell growth medium to which has been added a combination of hematopoietic growth factors and cytokines consisting essentially of interleukin-1, interleukin-3, interleukin-6, erythropoietin, stem cell growth factor, and interferon-γ.

8. The process of claim 7, wherein the peripheral blood cells are isolated by density gradient centrifugation.

9. The process of claim 7, wherein the peripheral blood cells are isolated by reaction with anti-CD34 monoclonal antibody, followed by immunoaffinity separation from non-reacted cells.

10. The process of claim 7, wherein the blood is obtained from a cancer patient.

11. The process of claim 10, wherein the cancer patient has received chemotherapy prior to the blood being obtained, the chemotherapy comprising administration of etoposide, isofamide and cisplatin.

12. The process of claim 11, wherein the prior chemotherapy is followed by combined or sequential administration of recombinant human interleukin-3 and recombinant human granulocyte-macrophage colony stimulating factor prior to the blood being obtained.

* * * * *